(12) United States Patent
Sakai (10) Patent No.: US 9,239,429 B2
(45) Date of Patent: Jan. 19, 2016

(54) FIBER SENSOR

(71) Applicant: OLYMPUS CORPORATION, Tokyo (JP)

(72) Inventor: Aiko Sakai, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/338,739

(22) Filed: Jul. 23, 2014

(65) Prior Publication Data

US 2014/0328557 A1 Nov. 6, 2014

Related U.S. Application Data

(63) Continuation of application No. PCT/JP2013/051636, filed on Jan. 25, 2013.

(30) Foreign Application Priority Data

Jan. 25, 2012 (JP) .................. 2012-013285

(51) Int. Cl.
*G02B 6/12* (2006.01)
*G02B 6/26* (2006.01)
*G01D 5/353* (2006.01)
(Continued)

(52) U.S. Cl.
CPC ............ *G02B 6/262* (2013.01); *A61B 1/00096* (2013.01); *A61B 1/00165* (2013.01); *A61B 1/07* (2013.01); *G01D 5/35367* (2013.01); *G02B 2006/12138* (2013.01)

(58) Field of Classification Search
CPC ........... A61B 19/5244; A61B 19/5212; A61B 2019/5261; A61B 5/0066; G01H 9/004
USPC ........................................................ 385/12
See application file for complete search history.

(56) References Cited

U.S. PATENT DOCUMENTS 5,633,494 A * 5/1997 Danisch ................... 250/227.16
6,420,696 B1 * 7/2002 Bennett et al. ........... 250/227.14
(Continued)

FOREIGN PATENT DOCUMENTS

EP         0 702 780 A1    3/1996
JP         8-511343 A     11/1996
(Continued)

OTHER PUBLICATIONS

International Search Report dated Mar. 5, 2013 issued in PCT/JP2013/051636.

(Continued)

*Primary Examiner* — Eric Wong
*Assistant Examiner* — Mary A El Shammaa
(74) *Attorney, Agent, or Firm* — Scully, Scott, Murphy & Presser, P.C.

(57) ABSTRACT

A fiber sensor includes a light source, and an optical fiber having flexibility to guide light emitted from the light source. The optical fiber has at least one light characteristics conversion portion. The fiber sensor also includes a light-receiving unit to receive the light guided by the optical fiber, and an identification unit having a unique shape on an outer peripheral surface of the optical fiber as compared with a round shape. The identification unit is formed to have a shape enabling at least one of an installation position and posture of the light characteristics conversion portion provided on the optical fiber to be identified.

11 Claims, 8 Drawing Sheets

(51) Int. Cl.
*A61B 1/00* (2006.01)
*A61B 1/07* (2006.01)

(56) References Cited

U.S. PATENT DOCUMENTS

2006/0285813 A1* 12/2006 Ferguson .................. 385/138
2007/0116415 A1   5/2007 Kobayashi

FOREIGN PATENT DOCUMENTS

| JP | 2001-169998 A | 6/2001 |
| JP | 2005-249861 A | 9/2005 |
| JP | 4005318 B2 | 11/2007 |
| JP | 2008-107145 A | 5/2008 |

OTHER PUBLICATIONS

English Abstract of JP 2002-253481 A, dated Sep. 10, 2002.
International Preliminary Report on Patentability with the Written Opinion dated Aug. 7, 2014 received in related International Application No. PCT/JP2013/051636, together with an English language translation dated Mar. 5, 2013.
Extended Supplementary European Search Report dated May 8, 2015 from related European Application No. 13 74 0976.9.
Chinese Office Action dated Aug. 4, 2015 from related Chinese Patent Application No. 201380006245.9, together with an English language translation.
Japanese Office Action dated Oct. 6, 2015 from related Japanese Patent Application No. 2012-013285, together with an English language translation.

* cited by examiner

F I G. 1

Light-guiding loss amount: large

F I G. 2A

Light-guiding loss amount: medium

F I G. 2B

Light-guiding loss amount: small

FIBER SENSOR

CROSS-REFERENCE TO RELATED APPLICATIONS

This is a Continuation Application of PCT Application No. PCT/JP2013/051636, filed Jan. 25, 2013, which was published under PCT Article 21(2) in Japanese.

This application is based upon and claims the benefit of priority from prior Japanese Patent Application No. 2012-013285, filed Jan. 25, 2012, the entire contents of which are incorporated herein by reference.

BACKGROUND OF THE INVENTION

1. Field of the Invention

The present invention relates to a fiber sensor for detecting bending of an optical fiber depending on a change in the amount of light (light amount).

2. Description of the Related Art

Fiber sensors have been known as devices for detecting bending and twisting of a subject having flexibility. The fiber sensors comprise light sources, optical fibers, and light-receiving units. The optical fibers generally have cylindrical shapes over the whole length.

For example, Japanese Patent No. 4005318 discloses a flexible endoscope device that is provided with a bending detection optical fiber comprising a plurality of light characteristics conversion portions (bending detection portions), for example. These light characteristics conversion portions are fine defective portions, such as light absorption portions, and light-guiding loss, portions. The detection optical fiber is arranged at a predetermined position on a surface of a sheet of a flexible band-like member. The bending detection portions are arranged in the longitudinal direction of the band-like member at predetermined intervals, and the same bending detection portions are arranged in parallel with each other.

The light characteristics conversion portions provided to the detection optical fiber have the function of causing a light loss depending on the direction and the degree of bending and twisting of a subject, such as an inserting-part flexible tube of the flexible endoscope. In other words, the direction and the degree of bending are detected depending on a change in the amount of light transmitted in at least one of the light characteristics conversion portions arranged in the longitudinal direction. Furthermore, if twisting occurs, the light characteristics conversion portions arranged in parallel with each other cause a difference in the amount of transmitted light, which causes the direction and the degree of twisting to be detected.

According to the aforementioned bending detection optical fibers, it is possible to determine the direction and the degree of bending and twisting of the subject by detecting a change in the amount of transmitted light. The bending detection optical fiber and the light characteristics conversion portions, therefore, need to be accurately arranged at specified positions.

BRIEF SUMMARY OF THE INVENTION

In accordance with an embodiment of the invention, a fiber sensor comprises: a light source; an optical fiber having flexibility that guides light emitted from the light source and comprises at least one light characteristics conversion portion; a light-receiving unit that receives the light guided by the optical fiber; and an identification unit that has a unique shape on an outer peripheral surface of the optical fiber as compared with a round shape, and that is formed to have a shape enabling at least one of an installation position and posture of the light characteristics conversion portion provided on the optical fiber to be identified.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Exemplary embodiments according to the present invention are described below with reference to the accompanying drawings.

The First Embodiment

Figure 1:
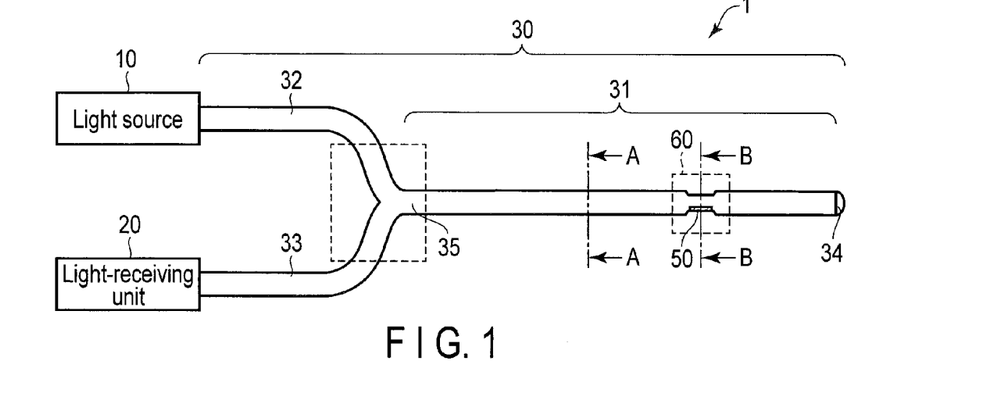
FIG. 1 is a schematic view illustrating the configuration of a fiber sensor in accordance with the first embodiment.

FIG. 1 is a schematic view illustrating the configuration of a fiber sensor 1 in accordance with the first embodiment.

The fiber sensor 1, as will be described later, is attached along a subject, such as a long and flexible member such that the fiber sensor 1 detects the bending state and the bending direction of the subject. When the fiber sensor 1 is attached to the subject, a light characteristics conversion portion 50 is installed at an appropriate position from the subject by positioning an identification unit 60 of the fiber sensor 1 using a bending part of the subject as a reference. Members to which the fiber sensor 1 is attached to are hereinafter referred to as the subject. The appropriate position means a designed or specified position, and is hereinafter referred to as a specified position.

The fiber sensor 1 in the first embodiment comprises a light source 10 emitting detection light, an optical fiber 30 having an elongated shape and guiding the light emitted from the light source 10, and a light-receiving unit 20 receiving the light guided by the optical fiber 30, as illustrated in FIG. 1. The light source 10 is, for example, a light-emitting diode (LED) or a laser light source. The optical fiber 30 comprises at least a core and may comprise a covering portion. The covering portion, for example, comprises a clad and/or a covering member.

The optical fiber 30 branches in three ways at an optical fiber coupling 35 dividing light into an introducing path and a deriving path, and comprises a fiber unit for detection 31, a fiber unit for supplying light 32, and a fiber unit for receiving light 33, which are respectively extended and formed into a Y-shape.

The fiber unit for supplying light 32 is the introducing path for the optical fiber 30 and guides the light emitted from the light source 10, which is provided at one end, to the optical fiber coupling 35.

The fiber unit for detection 31 follows a flexible operation of the subject and has an end surface (reflecting unit) 34 or other units for reflected light at a distal end so as to bounce the light back and forth. In other words, the fiber unit for detection 31 guides the light from the fiber unit for supplying light 32 passing through the optical fiber coupling 35 to the end surface 34, and guides the reflected light reflected at the end surface 34 back to the optical fiber coupling 35.

The fiber unit for receiving light 33 is the deriving path for the optical fiber 30 and guides the reflected light, which is reflected at the end surface 34 and branches into the optical fiber coupling 35, to the light-receiving unit 20 provided at the other end.

The fiber unit for detection 31 comprises the light characteristics conversion portion 50 serving as a bending detection portion and the identification unit 60 shaped to easily identify a position and a shape. With the fiber unit for detection 31 in the present embodiment, the installation position and posture of the light characteristics conversion portion 50 can be specified and installed using the identification unit 60.

The light characteristics conversion portion 50 in the present embodiment has the function of converting characteristics of the guided light. The light characteristics conversion portion 50 is, for example, a light-guiding loss portion or a wavelength conversion portion. If the light characteristics conversion portion 50 is, for example, a light-guiding loss portion, it is a light absorption body. If the light characteristics conversion portion 50 is, for example, a wavelength conversion portion, it is a phosphor and so on. In the present embodiment, the light characteristics conversion portion is considered as a light-guiding loss portion.

The identification unit 60 is provided to a predetermined portion of the fiber unit for detection 31 and has a predetermined length and width. The predetermined portion means a portion that is a target of detection of bending on the fiber unit for detection 31, and is, for example, a portion near the end surface 34 or a portion separated from the end surface 34 by an optional distance. The position of this portion, which will be described later, needs to be accurately recognized. A predetermined length and width of the light characteristics conversion portion is the length and width for changing the light amount in order to appropriately detect bending when the propagated light has reached this light characteristics conversion portion. In other words, the light characteristics conversion portion is a portion contacting the core and has an area sufficient for appropriately changing the light amount when the optical fiber is bent.

The identification unit 60 is shaped to have a cross-sectional shape different from that of the portion adjacent thereto. The cross-sectional shape is specified as the shape of a face perpendicular to the optical fiber 30 in the longitudinal direction. The cross-sectional shape of the optical fiber is usually round. For example, as illustrated in FIG. 1, the optical fiber 30 has a round cross-sectional shape on a cross section along line A-A, and has an oval cross-sectional shape on a cross section along line B-B of the identification unit 60. In this case, the cross-sectional shape other than that of the identification unit 60 is identical to that of the cross section along line A-A. The light characteristics conversion portion 50 and the identification unit 60 may be provided to the fiber unit for supplying light 32 and/or the fiber unit for receiving light 33. The light characteristics conversion portion 50 and the identification unit 60 may be each provided to a plurality of portions.

The light emitted from the light source 10 is guided through the fiber unit for supplying light 32, the optical fiber coupling 35, and the fiber unit for detection 31, and is reflected at the reflecting unit 34. The reflected light reflected at the reflecting unit 34 branches at the optical fiber coupling 35 as detection light, then, is guided through the fiber unit for receiving light 33 and reaches the light-receiving unit 20. The light-receiving unit 20 receives and photoelectrically converts the detection light and outputs an electrical signal indicating a light amount.

Figure 2A:
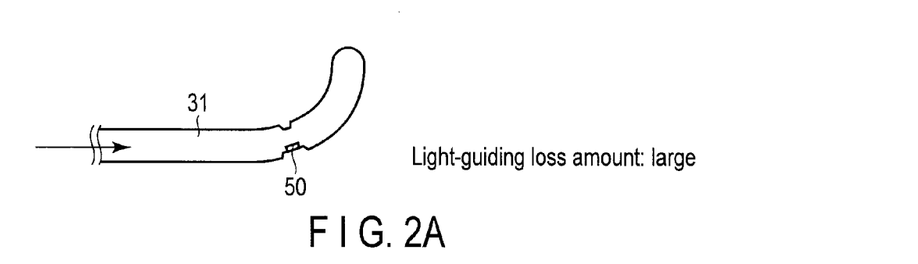
FIG. 2A is a schematic view illustrating an operation of the fiber sensor.
Figure 2B:
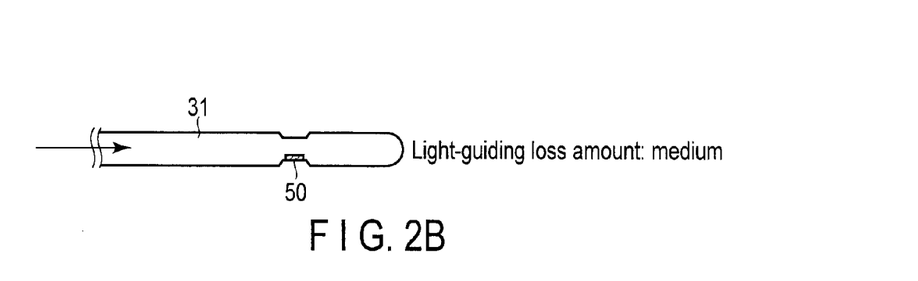
FIG. 2B is a schematic view illustrating an operation of the fiber sensor.
Figure 2C:
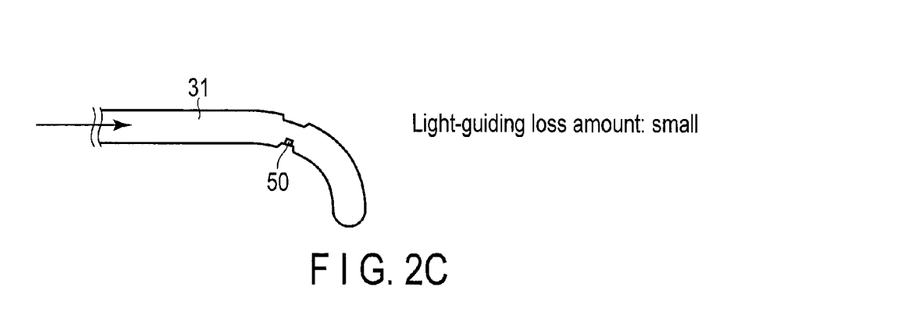
FIG. 2C is a schematic view illustrating an operation of the fiber sensor.

FIG. 2A, FIG. 2B, and FIG. 2C are schematic views illustrating operations of the fiber sensor 1.

In the present embodiment, a loss is caused in the detection light guided in the optical fiber 30 at the light characteristics conversion portion 50. This amount of loss in guided light varies depending on the direction and the amount of bending of the fiber unit for detection 31 as illustrated in FIGS. 2A to 2C.

In FIG. 2B, even if the fiber unit for detection 31 is in a straight state, a certain amount of the light is lost at the light characteristics conversion portion 50 based on the opening area of the light characteristics conversion portion 50. The amount of loss in light in this state is used as a reference. For example, as illustrated in FIG. 2A, when the light characteristics conversion portion 50 is outwardly arranged on the peripheral surface of the bending fiber unit for detection 31 in the bending direction, the amount of loss in guided light is more than the reference one in FIG. 2B. By contrast, as illustrated in FIG. 2C, when the light characteristics conversion portion 50 is inwardly arranged on the peripheral surface of the bending fiber unit for detection 31 in the bending direction, the amount of loss in guided light is less than the reference one in FIG. 2B.

This change in the amount of loss in guided light is reflected into the amount of detection light received by the light-receiving unit 20. In other words, the change is reflected into an output signal of the light-receiving unit 20. The output signal of the light-receiving unit 20 allows recognition of the bending direction and the bending amount (angle) of the fiber sensor 1, in other words, of the subject at a position corresponding to the light characteristics conversion portion 50.

In accordance with the present embodiment, the identification unit 60 is visually and tactually identified in the optical fiber having an elongated shape, thereby enabling devices and/or users to easily recognize the installation position and posture of the light characteristics conversion portion 50. In other words, the fiber unit 31 can be easily installed in a specified posture and at a specified position. The specified position, for example, indicates a bending part of the subject.

Figure 3:
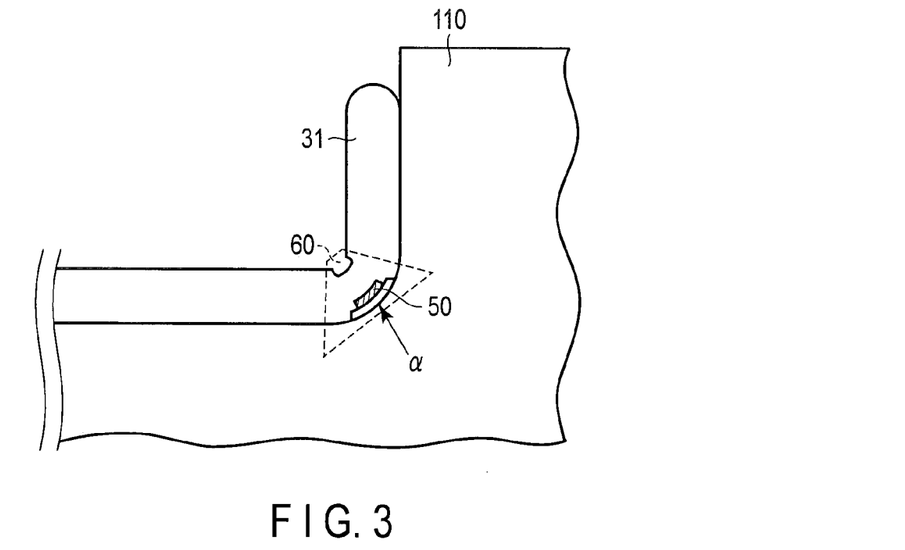
FIG. 3 is a view illustrating an example in which a fiber unit for detection provided to the fiber sensor in the first embodiment is attached to a member such as jigs serving as a subject.

FIG. 3 is a view illustrating an example in which the fiber unit for detection 31 provided to the fiber sensor in the present embodiment is attached to a subject 110, which is a member such as jigs.

In this example, the fiber unit for detection 31 has at least one bending part on the attached part thereof, and a mark a is assigned to the bending part. This mark a is used as a reference to position the fiber sensor, whereby the fiber sensor can be installed at the designed position. In other words, the identification unit 60 is attached to the bending position α of the subject 110, whereby the light characteristics conversion portion 50 of the fiber sensor 1 can be installed at the accurate installation position. Also, by providing a projection fitted to the identification unit 60, for example, at the bending position α, it is possible to easily and accurately attach the fiber unit for detection 31.

In addition, the installation posture of the fiber unit for detection 31 for the subject 110 can be easily specified. In other words, the fiber unit for detection 31 can be installed in a flexible posture and with ease in consideration of the installation position and posture of the light characteristics conversion portion 50. The installation position of the light characteristics conversion portion 50 means a predetermined portion of the fiber unit for detection 31, and indicates the position of an opening portion where light guided in the optical fiber leaks so as to cause a loss of the light. The installation posture of the fiber unit for detection 31 indicates, for example, an installation to which the following operations are added: the fiber unit for detection 31 is rotated in a circumferential direction and installed on the subject; the fiber unit for detection 31 is wound around the subject, or the like. The posture of the light characteristics conversion portion 50 means the opening direction of the opening portion thereof, in other words, the direction in which light lost from the optical fiber is emitted. The direction is not limited to a particular direction.

Also, the identification unit 60 can be utilized as a mark for a processing position when the light characteristics conversion portion 50 is processed (cut, or the like). Thus, the accuracy of installation processing of the light characteristics conversion past 50 is improved. This enables the characteristics conversion portion 50 to be installed and processed as designed, thereby enabling accurate recognition of the installation position of the light characteristics conversion portion 50.

The installation position of the identification unit 60 does not necessarily match that of the light characteristics conversion portion 50. For example, if the shape of the identification unit 60 is preliminarily associated with the position and/or posture of the light characteristics conversion portion 50, the position and posture of the light characteristics conversion portion 50 can be recognized.

The present embodiment limits no configuration or method for branching into and/or separating the detection light from the light source and the detection light to the light-receiving unit.

The present embodiment describes as an example a configuration example in which an optical fiber (optical fiber unit for detection) comprises an optical fiber coupling, has light reflected at an end surface (reflecting unit), and has light introduced and derived therein, but is not limited to this. It is a matter of course that the present embodiment can be easily applied to a light-guiding fiber sensor connecting a light source provided at one end of the fiber sensor and a light-receiving unit provided at the other end opposite to the light source, comprising an optical fiber guiding light emitted from the light source and the light-receiving unit, and having these components arranged in a straight line, for example.

The Second Embodiment

The following describes the second embodiment. A fiber sensor in the present embodiment is similar in configuration to the one in the first embodiment, but they are different in shape of identification units, for example.

In other words, the present embodiment describes an example of the shape of the identification portion 60 in FIG. 1. Identification units 60b, 60c, 60d, and 60e in the present embodiment have elements and positions similar to those of the identification portion 60 in FIG. 1. In the present embodiment, components similar to those in the first embodiment are denoted by the same reference numerals, and an overlapping explanation thereof will be omitted.

Figure 4A:
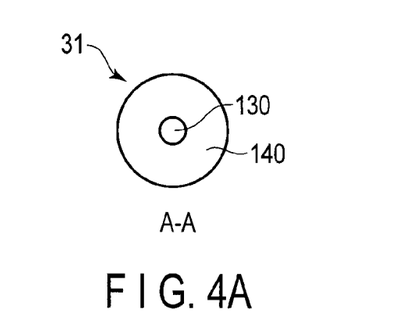
FIG. 4A is a view illustrating a cross section of an optical fiber in accordance with the second embodiment.

FIGS. 4A, 4B, 4C, 4D, and 4E are views illustrating cross sections of an optical fiber in accordance with the present embodiment, respectively. FIG. 4A illustrates a cross-sectional shape along line A-A in FIG. 1. FIGS. 4B, 4C, 4D, and 4E are views illustrating examples of a cross-sectional along line B-B of the identification unit 60 in FIG. 1.

The optical fiber of the present embodiment comprises any one of the identification portions 60b, 60c, 60d, and 60e with shapes different from that of the identification portion of the optical fiber in the first embodiment, which has a common configuration. Each of the identification portions 60b, 60c, 60d, and 60e comprises the corresponding one of the light characteristics conversion portions 50b, 50c, 50d, and 50e, a core 130 guiding light, and the corresponding one of the covering portions 140b, 140c, 140d, and 140e. The configuration of the core 130 is common to the identification units 60b, 60c, 60d, and 60e.

The light characteristics conversion portions 50b, 50c, 50d, and 50e are formed to match the outer peripheral shapes of the covering portions 140b, 140c, 140d, and 140e, respectively, and are provided in contact with the core 130. Each of the covering portions 140b, 140c, 140d, and 140e comprises at least one of a clad and a covering member. This enables each of the identification portions 60b, 60c, 60d, and 60e to be shaped without changing the cross-sectional shape of the core 130. The cross-sectional shape of the core 130 is round as an example, but is not necessarily round.

In the present embodiment, the part other than the identification portions 60b, 60c, 60d, and 60e shaped to have unique shapes in each optical fiber is shaped to have a round cross-sectional shape, as illustrated in FIG. 4A. In the optical fiber 30, the cross-sectional shape of the cross section along line B-B is shaped into a unique cross-sectional shape as compared with a round shape.

The following describes an example of the shape of the cross section along line B-B with reference to FIGS. 4B to 4E.

Figure 4B:
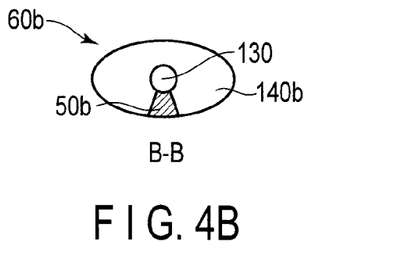
FIG. 4B is a view illustrating a cross-sectional shape of an identification unit of the optical fiber in the second embodiment.

FIG. 4B is a view illustrating the cross section along line B-B of the identification unit having an oval cross-sectional shape.

As illustrated in FIG. 4B, the identification unit 60b has the outer peripheral shape of the covering portion 140b shaped to have an oval cross-sectional shape. The covering portion 140 of the fiber unit for detection 31 has a round outer peripheral shape, thereby easily shaping the outer peripheral shape of the covering portion 140 into an oval shape. Even in this case, only the portion where the identification unit 60b is arranged has a different outer peripheral shape, thereby allowing the identification unit 60b to be easily identified.

The oval shape has a long axis and a short axis, thereby easily specifying a direction. This allows the installation posture of the optical fiber to be easily recognized. In other words, this allows the installation position and posture of the light characteristics conversion portion 50b to be easily recognized. The optical fiber can be installed in a specified posture by preliminarily recognizing that the opening portion of the light characteristics conversion portion 50b is installed facing the upper side of the oval shape, for example.

Figure 4C:
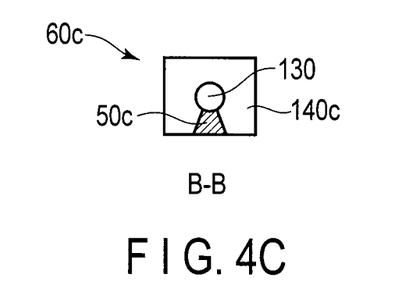
FIG. 4C is a view illustrating a cross-sectional shape of an identification portion of the optical fiber in the second embodiment.

FIG. 4C is a view illustrating the cross section along line B-B of the identification unit having a rectangular cross-sectional shape.

As illustrated in FIG. 4C, the identification unit 60c has the outer peripheral shape of the covering portion 140c shaped to have a rectangular cross-sectional shape. The outer periphery of the covering portion 140 of the optical fiber is processed (cut, or the like) into four sides, thereby easily providing the optical fiber with a rectangular cross section. Even in this case, only the portion where the identification unit 60c is provided in the longitudinal direction of the optical fiber has a different shape. This allows the identification unit 60 on the optical fiber to be easily identified.

In case that the shape is a rectangle, the rectangle has a long side and a short side, thereby easily specifying a direction. This allows the installation posture of the optical fiber 30 to be easily recognized. In other words, this allows the installation position and posture of the light characteristics conversion portion 50 to be easily recognized. The optical fiber 30 can be installed in a specified posture by preliminarily recognizing that, for example, the opening portion of the light characteristics conversion portion 50 is installed facing a long-side part or a short-side part of the rectangular cross section.

Figure 4D:
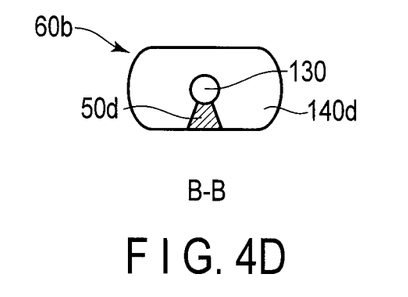
FIG. 4D is a view illustrating a cross-sectional shape of an identification portion of the optical fiber in the second embodiment.

FIG. 4D is a view illustrating the cross section along line B-B having a track (barrel) cross-sectional shape, which combines a round shape and a straight shape. The track shape or the barrel shape has a barrel cross-sectional shape combining two curved-face shapes and two plane shapes, and has parallel faces on the upper and lower sides in a cylindrical shape. The shape as illustrated in FIG. 4D is hereinafter referred to as a track shape. As illustrated in FIG. 4D, the identification unit 60d has the outer peripheral shape of the covering portion 140d shaped to have a track cross-sectional shape. Two sides in the outer periphery of the covering portion 140 of the fiber unit for detection 31 are processed (cut, or the like) into a plane face, thereby easily providing the optical fiber 30 with a track-shaped cross section. Even in such a shape, alternate plane and curved faces are in contact with each other. This allows the identification unit 60 on the optical fiber to be easily identified.

The track shape has a round-shaped part and a rectangular-shaped part so as to easily specify a direction using a plane-face part as a reference. This allows the installation posture of the optical fiber 30 to be easily recognized. In other words, this allows the installation position and posture of the light characteristics conversion portion 50 to be easily recognized. The optical fiber 30 can be installed in a specified direction by preliminarily recognizing that the light characteristics conversion portion 50 is installed in a predetermined part of the plane-face part or the curved-face part, for example.

Figure 4E:
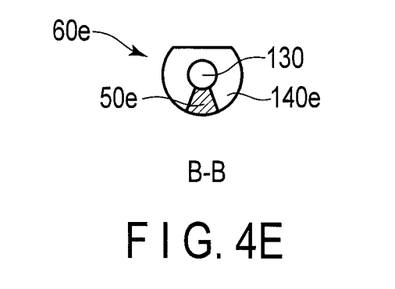
FIG. 4E is a view illustrating a cross-sectional shape of an identification portion of the optical fiber in the second embodiment.

FIG. 4E is a view illustrating the cross section along line B-B having a semi-cylindrical shape.

The semi-cylindrical shape is a shape which combines a cylindrical-face part with a plane-face part. As illustrated in FIG. 4E, the identification unit 60e has the outer peripheral shape of the covering portion 140e shaped to have a semi-cylindrical cross-sectional shape. The outer periphery of the covering portion 140 of the optical fiber 31 is processed (cut, or the like) to form two parallel plane faces, thereby easily providing the optical fiber 30 with a semi-cylindrical cross section. This shape, which has a plane-face part, allows the identification unit 60 on the optical fiber to be easily identified.

The plane-face part is defined as a reference face, thereby easily specifying a direction. This allows the installation direction of the optical fiber 30 to be easily recognized. In other words, this allows the installation position and posture of the light characteristics conversion portion 50 to be easily recognized. The optical fiber 30 can be installed in a specified direction by preliminarily recognizing that the light characteristics conversion portion 50 is installed in a predetermined position using the plane-face part as a reference, for example.

The present embodiment enables the identification unit 60b, 60c, 60d, or 60e to be easily processed (cut, or the like) from the optical fiber having a round cross-sectional shape. The identification unit 60b, 60c, 60d, or 60e is shaped to have a unique shape. This allows the installation position and posture of the optical fiber to be easily identified. In other words, this allows the installation position and posture of the light characteristics conversion portion 50 provided to the optical fiber to be easily recognized.

The cross-sectional shape of the identification unit 60 is not limited to the shapes described in the present embodiment. As long as the installation position, the opening direction, and the shape of the identification unit 60 are easily identified, the cross-sectional shape thereof is not limited to a particular shape.

The Third Embodiment

The following describes the third embodiment.

A fiber sensor in the third embodiment and the fiber sensors of the first and second embodiments are similar in configuration, but they are different in the arrangement and the number of components arranged, for example. In other words, the present embodiment describes an example of the arrangement and the number of components arranged of the identification unit 60 of the optical fiber 30 in FIG. 1. Optical fibers 30a, 30b, 30c, and 30d have elements and positions similar to those of the optical fiber 30 in FIG. 1. In the present embodiment, components similar to those of the first embodiment are denoted by the same reference numerals, and an overlapping explanation thereof will be omitted.

FIGS. 5A, 5B, 5C, and 5D are views illustrating different arrangement examples of identification units 61, 62, 63, and 64 of the optical fibers 30a, 30b, 30c, and 30d, respectively, in accordance with the present embodiment.

The fiber sensor in the present embodiment comprises a light source, any one of the optical fibers 30a, 30b, 30c, and 30d, and a light-receiving unit. The optical fibers 30a to 30d each comprise a core and a covering portion.

Figure 5A:
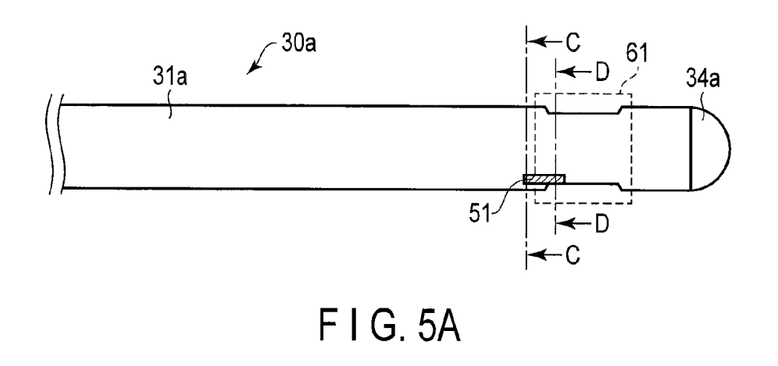
FIG. 5A is a view illustrating an arrangement example of an identification portion of each optical fiber in accordance with the third embodiment.
Figure 6A:
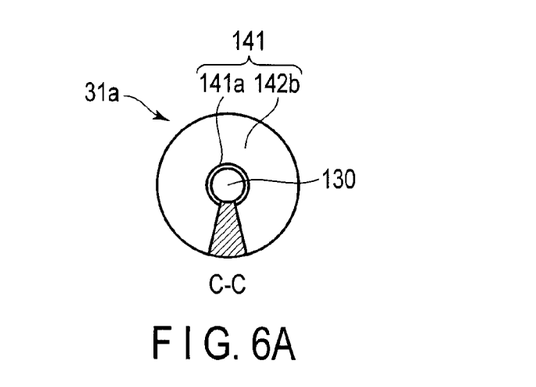
FIG. 6A is a view illustrating a cross-sectional shape of the optical fiber in the third embodiment.
Figure 6B:
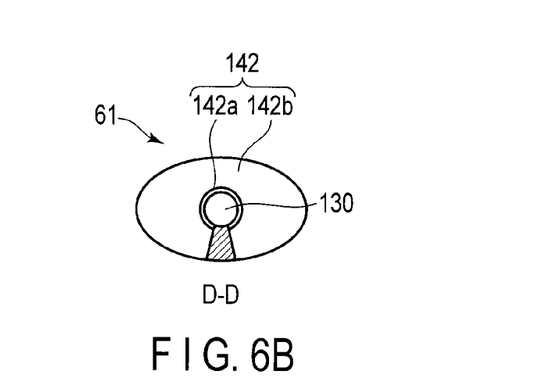
FIG. 6B is a view illustrating a cross-sectional shape of the identification portion of the optical fiber in the third embodiment.
Figure 7A:
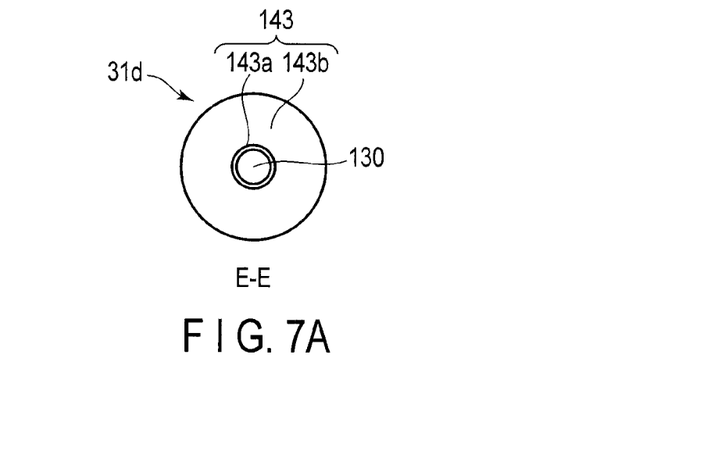
FIG. 7A is a view illustrating an example cross-sectional shape of the optical fiber in the third embodiment.
Figure 7B:
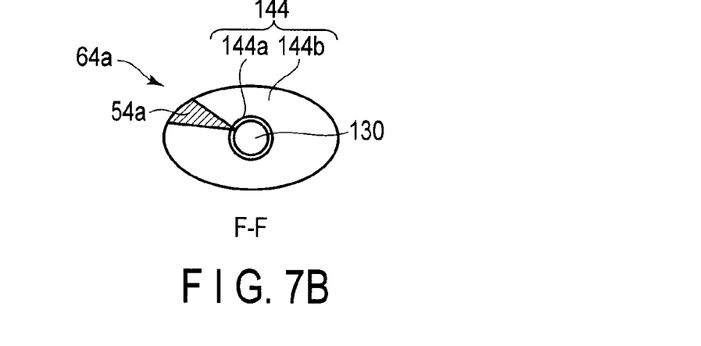
FIG. 7B is a view illustrating an example cross-sectional shape of each identification portion of the optical fiber in the third embodiment.
Figure 7C:
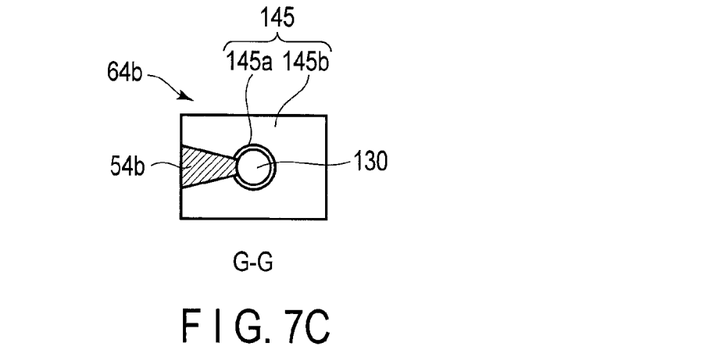
FIG. 7C is a view illustrating an example cross-sectional shape of each identification portion of the optical fiber in the third embodiment.
Figure 7D:
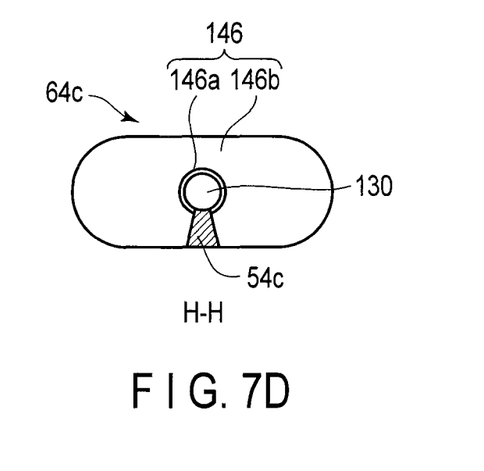
FIG. 7D is a view illustrating an example cross-sectional shape of each identification portion of the optical fiber in the third embodiment.

FIG. 6A is a view illustrating an example cross-sectional shape of an optical fiber along line C-C in the present embodiment. FIG. 6B is a view illustrating an example cross-sectional shape of an identification unit along line D-D of the optical fiber in the present embodiment. FIG. 7A is a view illustrating an example cross-sectional shape of an optical fiber along line E-E in the present embodiment. FIGS. 7B, 7C, and 7D are views illustrating examples of cross-sectional shapes of the respective identification units of the optical fiber in the present embodiment. For example, as illustrated in FIG. 6A, A covering portion 141 comprises a clad 141a and a covering member 141b. Similarly, as illustrated in FIG. 6A, a covering portion 142 having the identification portion's cross section along line D-D of the optical fiber in FIG. 5A comprises a clad 142a and a covering member 142b. Furthermore, as illustrated in FIGS. 7A to 7D, covering portions 143, 144, 145, and 146 comprise clads 143a, 144a, 145a, and 146a, and covering members 143b, 144b, 145b, and 146b, respectively. The covering portions 141 to 146 share the configuration. The cross-sectional shapes illustrated in FIGS. 7A to 7D are just examples, and may be other shapes. The covering portions 141 and 142, or the covering portions 143 to 146 may have different shapes or may have the same shape. When having the same shape, for example, the covering portions are shaped to have different diameters so as to be identified.

In the present embodiment, the cross-sectional shape of each optical fiber is round in the portion other than the identification units 61, 62, 63, or 64. The shape of each optical fiber and the respective cross-sectional shapes of the identification units 61 62, 63, and 64 illustrated in FIGS. 5A to 5D may be different, and may be the same as long as they can be identified.

Each of the optical fibers 30a, 30b, 30c, and 30d comprises a fiber unit for supplying light, the corresponding one of the fiber units for detection 31a, 31b, 31c, and 31d, a fiber unit for receiving light, an optical fiber connection, and the corresponding one of the reflecting units 34a, 34b, 34c, and 34d. The fiber unit for supplying light, the fiber unit for receiving light, and the optical fiber connection are not illustrated. The reflecting units 34a to 34d each share the configuration with the reflecting unit 34 in the first embodiment.

Each of the fiber units for detection 31a, 31b, 31c, and 31d comprises the corresponding one of the light characteristics conversion portions 51, 52, 53, and 54, and the corresponding one of the identification units 61, 62, 63, and 64. The light characteristics conversion portions 51 to 54 and the identification units 61 to 64 may be each provided to the fiber unit for supplying light and/or the fiber units for detection. The light characteristics conversion portions 51 to 54 are each installed in contact with a core 130.

The optical fibers 30a to 30d are each shaped to have unique cross-sectional shapes at the identification units 61 to 64 as compared with a round shape. For example, as illustrated in FIG. 6B, the covering portion 142 of the identification unit 61 comprises the clad 142a and the covering member 142b. The covering member 142b of the identification portion 61 is shaped to have an oval outer peripheral shape, which is different from the round shape in FIG. 6A.

The cross-sectional shapes of the identification portions 61 to 64 are formed into determinable shapes such as the cross-sectional shapes illustrated in the second embodiment. For example, the respective cross-sectional shapes of the identification portions 61 to 64 are formed into an oval, a rectangular, a track, or a semi-cylindrical shape. In the present embodiment, the cross-sectional shape of the core 130 is completely round over the whole length of the optical fiber in order not to change light propagation characteristics. Each cross-sectional shape of the identification units 61 to 64 has an equal cross-sectional area to that of the portion other than the identification units 61 to 64.

The following describes the arrangements of the identification units 61 to 64.

FIG. 5A is a view illustrating the arrangement of the identification unit provided on a portion of the outer periphery of the optical fiber.

As illustrated in FIG. 5A, in the optical fiber 30a, the identification portion 61 is shaped on the outer periphery of the optical fiber 30a so as to contact at least a portion of the installation position of the light characteristics conversion portion 51. For example, as illustrated in FIGS. 6A and 6B, cross-sectional shapes may be different or may be the same between the cross section along line C-C and the cross section along line D-D of the installation position of the light characteristics conversion portion 51. When the cross-sectional shapes are the same, the light characteristics conversion portion 51 is shaped, for example, to have a different diameter of the cross section, thereby being identified from the other portions in the optical fiber.

This arrangement allows the installation position and posture of the light characteristics conversion portion 51 to be recognized. The identification unit 61 can be used as a mark, for example, when the light characteristics conversion portion 51 is processed (cut, or the like) in the optical fiber 30a. The identification portion can be applied as a mark for processing (cutting, or the like) the light characteristics conversion portion in the above-mentioned and after-mentioned embodiments. The shape of the identification unit 61 is changed depending on the installation position and/or posture of the light characteristics conversion portion 51 in the optical fiber so as to recognize the installation posture of the light characteristics conversion portion 51 on the cross section of the optical fiber 30a. For example, when the identification unit 61 has an oval shape in FIG. 6B, the optical fiber 30a can be installed in a specified posture depending on the shape of the identification unit 61 by preliminarily recognizing that the opening portion of the light characteristics conversion portion 51 is provided facing the lower side of the oval shape. In this case, the direction of the optical fiber 30a is easily specified and the optical fiber 30a can be installed in a posture matching a subject (not illustrated).

Figure 5B:
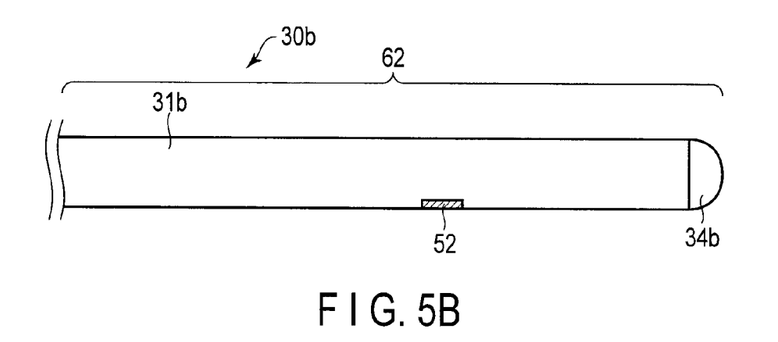
FIG. 5B is a view illustrating another arrangement example of an identification portion of each optical fiber in the third embodiment.

FIG. 5B is a schematic view illustrating the optical fiber 30b.

As illustrated in FIG. 5B, the identification unit 62 is installed over the whole length of the optical fiber 30b. In other words, the optical fiber 30b has the same cross-sectional shape over the whole length. The posture of the light characteristics conversion portion 52 is, therefore, specified for each shape so as to easily recognize the posture of the light characteristics conversion portion 52.

The same shape over the whole length facilitates processing of the optical fiber 30b. The direction of the optical fiber 30b is easily specified and the optical fiber 30b can be installed in an posture matching a subject (not illustrated).

Figure 5C:
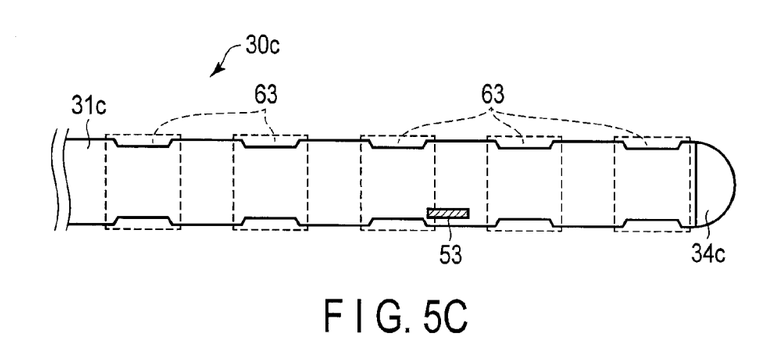
FIG. 5C is a view illustrating another arrangement example of an identification portion of each optical fiber in the third embodiment.

FIG. 5C is a schematic view illustrating the optical fiber 30c where a plurality of identification portions 63 are provided at different positions on the outer peripheral surface.

As illustrated in FIG. 5C, the cross-sectional shapes of the identification units 63 are formed to be identical. The identification units 63 are provided at different positions and at equal intervals. In the present embodiment, one light characteristics conversion portion 53 is installed for a plurality of identification units 63, and the posture of the light characteristics conversion portion 53 can be easily recognized by identifying any of the identification units 63 provided on the outer periphery of the optical fiber 30c. Therefore, the posture of the light characteristics conversion portion 53 is specified for each shape in association with the shapes of the identification units 63, thereby easily recognizing the posture of the light characteristics conversion portion 53. For example, if the light characteristics conversion portion 53 is installed so as to contact any position of the identification units 63 counted from the ends, the position of the light characteristics conversion portion 53 can be easily recognized as well. Furthermore, the direction of the optical fiber 30c is easily specified and the optical fiber 30c can be installed in an posture matching a subject (not illustrated). contain FIG. 5D is a schematic view illustrating the optical fiber 30d where the different light characteristics conversion portions 54 are arranged at different positions and postures for each cross-sectional shape.

The fiber unit for detection 31d comprises a plurality of identification units 64a, 64b, and 64c, and a plurality of light characteristics conversion portions 54a, 54b, and 54c. The identification units 64a to 64c are each provided on the outer periphery of the optical fiber 30d so as to be contained in at least a part of the installation range of the light characteristics conversion portions 54a to 54c. The identification units 64 have different shapes.

Figure 5D:
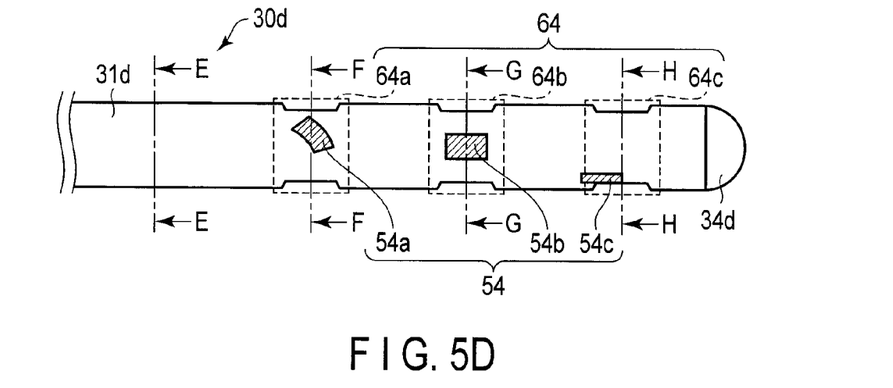
FIG. 5D is a view illustrating another arrangement example of an identification portion of each optical fiber in the third embodiment.

For example, FIG. 7A is a view illustrating a cross-sectional shape along line E-E in FIG. 5D. As illustrated in FIG. 7A, the portion other than the identification units 64 has a round shape in the optical fiber 30d. FIG. 7B is a view illustrating a cross-sectional shape along line F-F of the identification portion 64a in FIG. 5D. The cross section along line F-F of the identification unit 64a is oval. FIG. 7C is a view illustrating a cross-sectional shape along line G-G of the identification portion 64b in FIG. 5D. The cross section along line G-G of the identification unit 64b is rectangular. FIG. 7D is a view illustrating a cross-sectional shape along line H-H of the identification unit 64c in FIG. 5D. The cross section along line H-H of the identification portion 64c is track-shaped. In this manner, the corresponding covering portions 144 to 146 of the identification units 64a to 64c are shaped to have different outer peripheral shapes in the fiber unit for detection 31d.

The respective positions and postures of the light characteristics conversion portions 54 can be easily recognized depending on the positions and shapes of the identification units. In other words, each installation position of the light characteristics conversion portions 54 in the longitudinal direction can be easily identified depending on the positions of the identification units 64. The respective installation positions and postures of the light characteristics conversion portions 54 can be easily identified depending on the respective shapes of the identification units 64.

When each arrangement portion of the light characteristics conversion portions 54 comprises only a point with a shape different from that of the adjacent portion in the optical fiber in the longitudinal direction, the postures of the identification units 64 can be more accurately recognized. For example, if the identification units 64 have semi-cylindrical cross-sectional shapes and the adjacent portion has a round shape, the installation posture of the light characteristics conversion portions can be accurately recognized by installing the light characteristics conversion portions on a plane-face part of a semi-cylindrical shape. In this case, the direction of the optical fiber 30d is easily specified and the optical fiber 30d can be installed in a posture matching a subject (not illustrated).

In the present embodiment, the positions and postures of the light characteristics conversion portions 51 to 54 can be more easily recognized depending on the arrangements of the identification units 61 to 64.

The present embodiment limits no arrangement of the identification units. As long as an arrangement allows the identification units to be easily identified, any arrangement can be adopted.

The Fourth Embodiment

The following describes the fourth embodiment.

A fiber sensor in the fourth embodiment and the fiber sensors in the first to third embodiments are similar in configuration, but they are different in function and shape of each identification unit, for example. In the present embodiment, components similar to those of the first embodiment are denoted by the same reference numerals, and an overlapping explanation thereof will be omitted.

An identification unit 65 in the present embodiment comprises a recess fixed by a fitting member, a clamping member, or the like so that the identification unit 65 is more easily fitted to or clamped by a subject than the identification units in the above-mentioned embodiments are. A reflecting unit 340 in the present embodiment shares configuration components with the reflecting unit 34 in the first embodiment.

Figure 8:
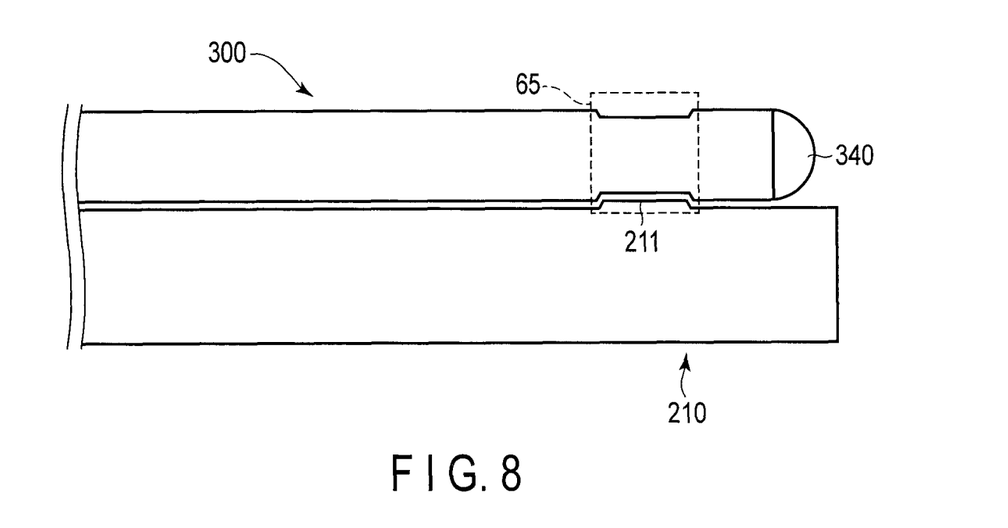
FIG. 8 is a view in which an optical fiber is fitted in accordance with the fourth embodiment.

FIG. 8 is an installation view of an optical fiber 300. When installed on a subject 210 comprising a protrusion 211, which is a fitting member, the optical fiber 300 allows the identification unit 65 to be fitted to or to be brought in contact with the protrusion 211, and to be installed. The identification unit 65 is used as a mark for the fitted portion or the contacted portion. Recesses and protrusions may be reversed between the identification unit 65 and the subject. Similarly, in the above-mentioned embodiments, for example, the identification portion may have a track-like shape projecting from a round cross-sectional shape of the optical fiber other than the identification portion. If the identification unit 65 comprises a protrusion, the identification unit 65 is installed on a subject comprising a recess, which is a fitting member, but is not applied to a subject comprising a clamping member.

Figure 9A:
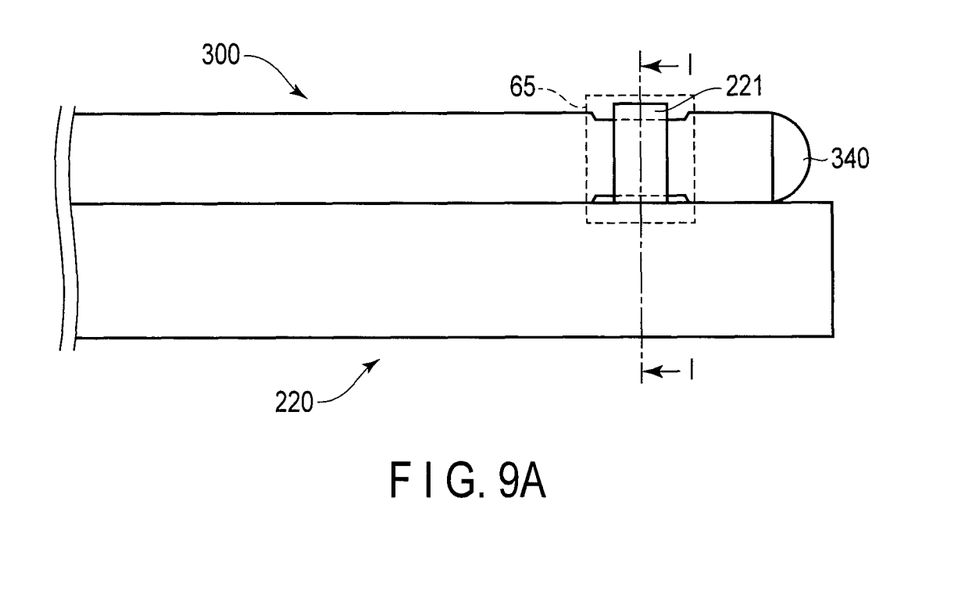
FIG. 9A is a view in which the optical fiber is clamped in the fourth embodiment.
Figure 9B:
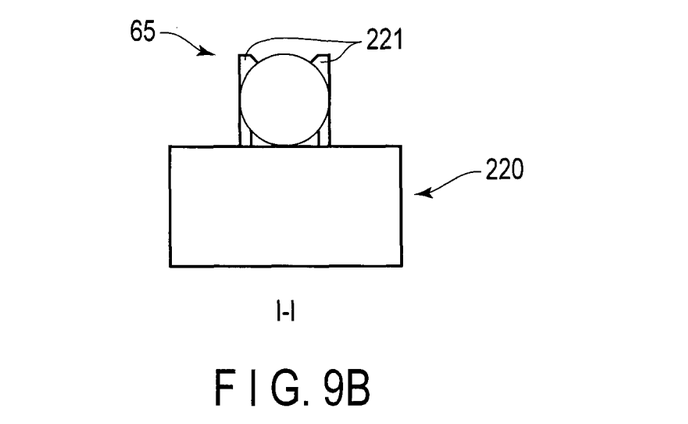
FIG. 9B is a view in which the optical fiber is clamped in the fourth embodiment.

FIGS. 9A and 9B are installation views of the clamped optical fiber 300 in the present embodiment. When the optical fiber 300 is installed on a subject 220 comprising a clamping portion 221, the identification unit 65 can be used as a fixing point. The identification unit 65 is also used as a mark for a clamped portion.

The present embodiment enables the optical fiber 300 to be accurately and surely installed on the subject 210 or 220 comprising a fitting member or a clamping member. Therefore, detection accuracy of the fiber sensor is improved by the identification unit 65 comprising a recess, which is fixed with a fitting member, a clamping member, or the like.

A plurality of identification units 65 having recesses, which are fixed with fitting members, clamping members, or the like, may be provided. The installation position of the identification unit 65 may contact the reflecting unit 340.

The embodiments described above limit no shape and arrangement of the fiber sensor.

What is claimed is:

1. A fiber sensor comprising:
   a light source;
   an optical fiber having flexibility that guides light emitted from the light source along an optical path, the optical fiber comprising light characteristics conversion portions, the light characteristics conversion portions being provided at different positions on the optical fiber in a longitudinal direction;
   a light-receiving unit that receives the light guided by the optical fiber; and
   the optical fiber further including identification units that are arranged to correspond to the light characteristics conversion portions respectively, the optical fiber corresponding to each of the identification units having a cross-sectional shape orthogonal to the optical path different from a cross-sectional shape orthogonal to the optical path of an adjacent portion of the optical fiber, wherein each of the cross-sectional shapes of the optical fiber corresponding to the identification units are formed to enable identification of at least one of an installation position and posture of the light characteristics conversion portions provided on the optical fiber.

2. The fiber sensor according to claim 1, wherein a shape of the identification units are preliminarily associated with at least one of the installation position and posture of the respective light characteristics conversion portions so as to recognize a relation between the shape of the identification units and at least one of the installation position and posture of the respective light characteristics conversion portions.

3. The fiber sensor according to claim 1, wherein at least one of the identification units comprises a plane-face part on an outer peripheral side surface of the optical fiber, the plane-face part enabling at least one of the installation position and posture of the respective light characteristics conversion portions to be recognized.

4. The fiber sensor according to claim 3, wherein at least one of the identification units is shaped to have a part of a cylindrical outer peripheral shape of the optical fiber formed into the plane-face part.

5. The fiber sensor according to claim 3, wherein a posture of the optical fiber provided with the light characteristics conversion portions and a direction in which the plane-face part is provided are identical or opposite to each other.

6. The fiber sensor according to claim 3, wherein at least one of the identification units is shaped to contact a part of the installation position of the respective light characteristics conversion portions.

7. The fiber sensor according to claim 1, wherein at least one of the identification units is shaped to be contained in a part of the installation position of the respective light characteristics conversion portions.

8. The fiber sensor according to claim 1, wherein the plurality of identification units are provided on the outer peripheral surface of the optical fiber.

9. The fiber sensor according to claim 8, wherein the identification units are shaped to have directions thereof aligned.

10. The fiber sensor according to claim 1, wherein the at least one of the identification units is fixed to a subject by a fitting member or a clamping member provided in the subject.

11. The fiber sensor according to claim 10, wherein one of the subject and at least one of the identification units comprises a protrusion on a part thereof and the other comprises a recess on a part thereof, and
   the at least one identification unit is fixed to the subject by the recess and the protrusion.

* * * * *